United States Patent [19]

Peterson et al.

[11] Patent Number: 4,530,907

[45] Date of Patent: Jul. 23, 1985

[54] PERFUSION-CULTIVATION OF ANIMAL CELLS AND EQUIPMENT THEREFOR

[76] Inventors: Anders Peterson, Petrusstugan, Askartorp, 150 11 Björnlunda; Erik Walum, Knipvägen 57, 184 00 Åkersberga, both of Sweden

[21] Appl. No.: 448,996
[22] PCT Filed: Feb. 19, 1982
[86] PCT No.: PCT/SE82/00050
 § 371 Date: Nov. 10, 1982
 § 102(e) Date: Nov. 10, 1982
[87] PCT Pub. No.: WO82/03227
 PCT Pub. Date: Sep. 30, 1982

[30] Foreign Application Priority Data

Mar. 12, 1981 [SE] Sweden .............................. 8101564

[51] Int. Cl.³ .................... C12N 5/00; C12M 3/04; C12M 1/22
[52] U.S. Cl. .................................. 435/240; 435/285; 435/297
[58] Field of Search .............. 435/240, 241, 284, 285, 435/286, 297, 298, 809

[56] References Cited

U.S. PATENT DOCUMENTS

| | | | |
|---|---|---|---|
| 2,701,229 | 2/1955 | Scherr | 435/298 |
| 3,591,461 | 7/1971 | Bazil et al. | 435/298 |
| 4,087,327 | 5/1978 | Feder et al. | 435/240 |
| 4,195,131 | 3/1980 | Papas | 435/240 X |
| 4,301,252 | 11/1981 | Baker et al. | 435/809 X |

FOREIGN PATENT DOCUMENTS

WO82/03227  9/1982  PCT Int'l Appl. ................ 435/286

OTHER PUBLICATIONS

Chemical Abstracts, vol. 85, 117685y; 1976.
Chemical Abstracts, vol. 87, 34017x; 1977.
Chemical Abstracts, vol. 88, 146838t; 1978.
G. F. Mann, *Develop. Biol. Standard*, vol. 37, pp. 149–152; 1977.
George H. Rothblatt and Vincent J. Cristofalo, Editors, *Growth, Nutrition, and Metabolism of Cells in Culture*, vol. II, pp. 11–25; 1972.
Michael J. Harvey and Raghubir P. Sharma, *Toxicol. Applied Pharmacol.*, vol. 45, pp. 232–233; 1978.

Primary Examiner—Robert J. Warden
Assistant Examiner—Randall E. Deck
Attorney, Agent, or Firm—Dennison, Meserole, Pollack & Scheiner

[57] ABSTRACT

The invention aims at replacing animal experiments for determining acute toxicity ($LD_{50}$ values) by utilizing stable perfusion-cultivated cell cultures and also at producing a cultivation chamber which is movable during operation, for determining various parameters.

14 Claims, 8 Drawing Figures

PERFUSION-CULTIVATION OF ANIMAL CELLS AND EQUIPMENT THEREFOR

The invention relates to a method of producing stable perfusion-cultivations of animal cells in a specially designed system, thereby determining toxicity, and apparatus for performing the method.

Requirements for improved working environment, combined with the rapidly increasing number of chemical substances in working life and in society in general has increased the need for toxicological examination. Such examination is normally performed by means of animal experiments which, however, are expensive, time-consuming and require considerable resources. The determination of acute toxicity ($LD_{50}$ values) on all the substances in question requires such vast resources that it is in practice difficult to achieve. The objection can also be raised that these experiments constitute cruelty to animals.

Attempts have been made to achieve mathematical models and store information in computers as to how an organ or a system of organs reacts in various situations, the computer subsequently simulating the toxic action of the substances tested, on the basis of this information. In biochemical models, the action of the chemical substance is tested on isolated biologically active substances, i.e. substances such as enzymes which control the chemical process in plants and animals which is the basis of all life. However, these mathematical and chemical models are uncertain and it is difficult to obtain reliable values of acute toxicity with them. The microbiological methods (Ames tests) are mostly used to determine the mutagenity of the substances, and thus their ability to cause cancer.

A simpler and less expensive method is thus required for determining the toxicity, and such a method has been effected according to the invention by means of stable perfusion-cultivations of animal cells in a specially designed apparatus giving laminar flow of the substrate.

Cultivation of cell cultures is performed by keeping isolated cells from animals and humans alive and cultivating them outside the body. The most usual type of cultivation is when the cells are placed in a dish or glass or plastic and surrounded by a substrate similar in composition to the body liquids. A test substance can be added to the cultivation substrate and changes in the cells be measured. The concentration of the substance which gives a certain defined alteration (in appearance, growth rate, size, $O_2$ absorption, enzyme activity, or ratio between living and dead cells, for instance) constitutes a gauge of the toxic activity in the cell culture. A great advantage with cell cultures is that they enable tests on human material since cultures can be started from cells in blood samples, amniotic fluid or surgically removed tissues, for instance.

When a cell culture is used for studying biochemical processes, it is important that cultivation occurs in a well defined environment. Perfusion cultivation enables this, providing the cultivation equipment used allows a uniform supply of nutrient. The flow properties of the cultivation chamber are important.

If it were possible to keep the perfusion cultivations stable, they could be used for fundamental biochemical studies of various animal cells, in medical research and for determining acute toxicity, for instance. To enable cell cultures to be used for following up biochemical processes, the cultivation must take place under extremely stable conditions and so far it has not been possible to achieve this in a satisfactory manner.

According to the invention, stable perfusion cultures are achieved by means of a specially designed apparatus which gives an extremely uniformly, substantially laminar flow. In the following the method and apparatus will be described with reference to seven drawings in which

FIG. 1C is a schematic cross-sectional view of a perfusion device according to the invention.

DESCRIPTION OF TEST SYSTEM

The test system in question is based on cultivation of neuroblastoma cells C1300, $41A_3$ and the effect on these cells measured as general biological cell changes or biochemical changes, as a function of the content of toxic substances in the substrate. The cell line used is suitable for such measurements since its biology and biochemistry is well documented.

The parent culture is cultivated in what are known as Costar plastic bottles in a commercial substrate Ham's F10 which includes 9% serum from new-born calf and 4% foetal calf serum.

DESCRIPTION OF THE TEST APPARATUS

Figure 1A:
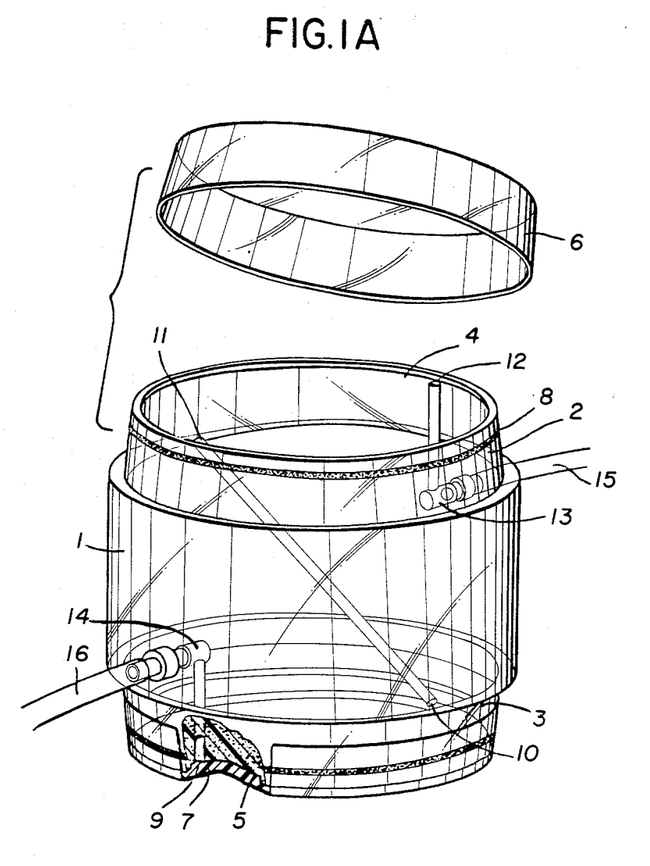
FIGS. 1A and 1B are perspective views of a perfusion device according to the invention.

The test apparatus according to FIG. 1A and shown schematically in FIG. 1C, comprises a body 1 made of polycarbonate. The body has a turned truncated cone 2,3 at each end. At the top of each cone is a turned recessed end surface 4,5, the depth of this recess determing the cultivation volume of the perfusion chamber. A cell dish 6,7 with the lid removed is pushed over the turned cone 2,3. The cone 2,3 has the same outer diameter as the inside of the bottom of the dish. An O-ring 8, suitably of fluorine or silicon rubber, is provided to seal between the body 1 and the cultivation dishes 6,7.

By placing cultivation dishes 6, 7 over the cones 2, 3, perfusion-cultivation chambers 50, 60 are formed.

Medium is supplied to or removed from the chamber through holes 9,10,11,12 drilled in the periphery of the recess 4,5. The direction of medium flow is shown by the arrows in FIG. 1C. Experiments with coloured solutions show that the flow is substantially laminar. Since the chamber is made of transparent material, it can be used in assembled state for light-microscopic studies.

Connections 13,14 of Luer type are arranged to the chamber, and to these are connected hoses 15, 16 of silicon rubber, to enable satisfactory acidification of the substrate by means of diffusion.

The following criteria are valid for the perfusion chamber:

(1) The cells are sown and cultivated in their normal environment; in this case in Falcon culture dishes in a culture incubator of conventional type.

(2) The chamber is simple, practical and robust to handle. Loose washers, screws, glass, etc, is eliminated.
(3) It can be autoclaved.
(4) It is inexpensive and simple to manufacture.
(5) It is suitable for light-microscopic studies
(6) It can be used in most types of perfusion applications.

As mentioned previously, it is important that the flow in the perfusion cell is substantially laminar so that the cell's biochemical activity is not disturbed by turbulent flow. The flow in the cell is determined by the channels in the cell and their diameter and extension in the perfusion cell. The following diameters, for instance, have been found suitable. See FIG. 1.

9: 2.0 mm
10: 2.0 mm
11: 2.0 mm
12: 2.0 mm
13: 4.0 mm
14: 4.0 mm

For good flow geometry, it is also important that the channel 10-11 has an angle of about 50°-55° to the horizontal plane. These measurements are applicable for an apparatus with double chamber and a cell diameter of 46 mm as in FIG. 1, and for the normal flow rate of about 1 ml/min. A lamina flow can be ensured by regulating the flow rate.

The body and the chamber may have a different appearance, deviating from FIG. 1, but the apparatus shall include a closed space for the perfusion chamber.

With the apparatus described, perfusion technique can be utilized in an extremely simple manner for biological cell studies and this is to a great extent because the dish forms a part of the assembled chamber. The cells need not be removed and transferred to a different surface, but can grow on their normal surface, in an environment which can be kept constant thanks to the perfusion technique. Due to its simple design, it should be possible to manufacture the apparatus relatively cheaply, thus enabling increased use of perfusion technique for biological cell studies. The apparatus is connected in a simple manner by means of hoses and can easily be moved to different measuring points.

To summarize, it can be established that the apparatus described is simple in design, ordinary cell cultivating dishes are used, it should be possible to produce it relatively cheaply, it has been found to have good through-flow properties, it is suitable for microscopic studies and it has been found useful in practice in a number of toxicological and general biological cell studies.

Figure 1B:
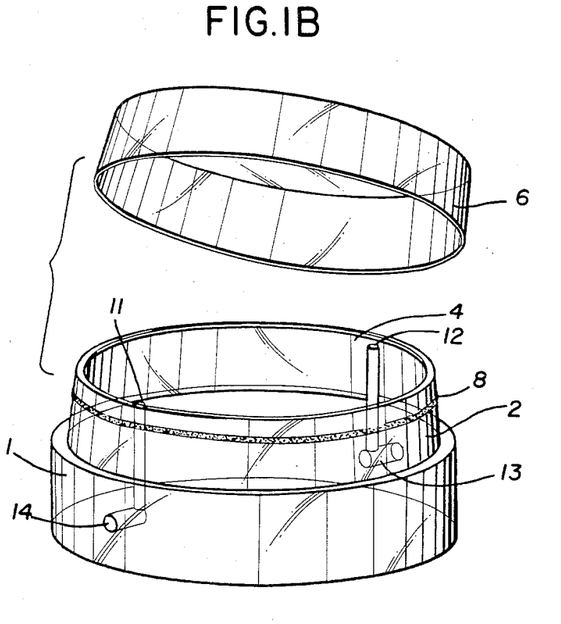

FIG. 1B shows a body 1 for perfusion of only one dish 6.

Figure 2:
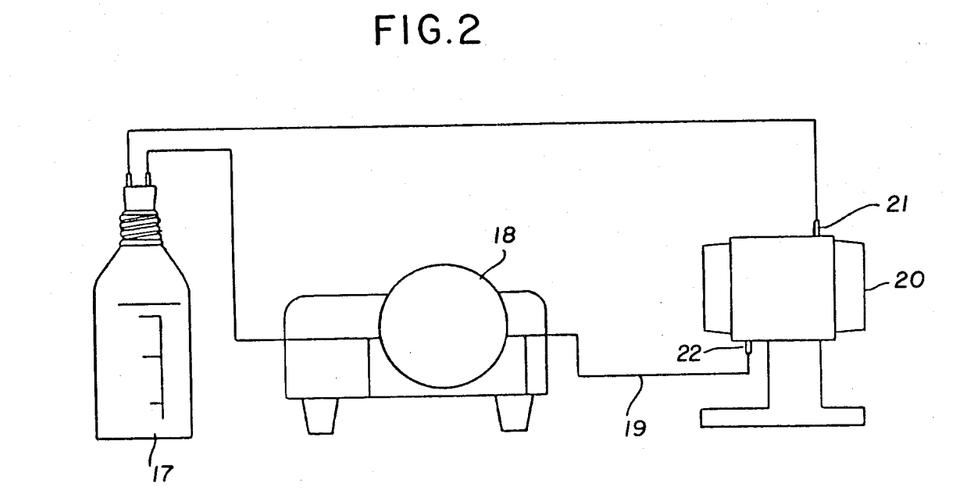
FIG. 2 shows how the apparatus is connected.

FIG. 2 shows how the apparatus is connected. The medium is pumped by a pump 18 from a store 17 through hoses 19 to the perfusion chamber 20 via connections 21,22.

Figure 3:
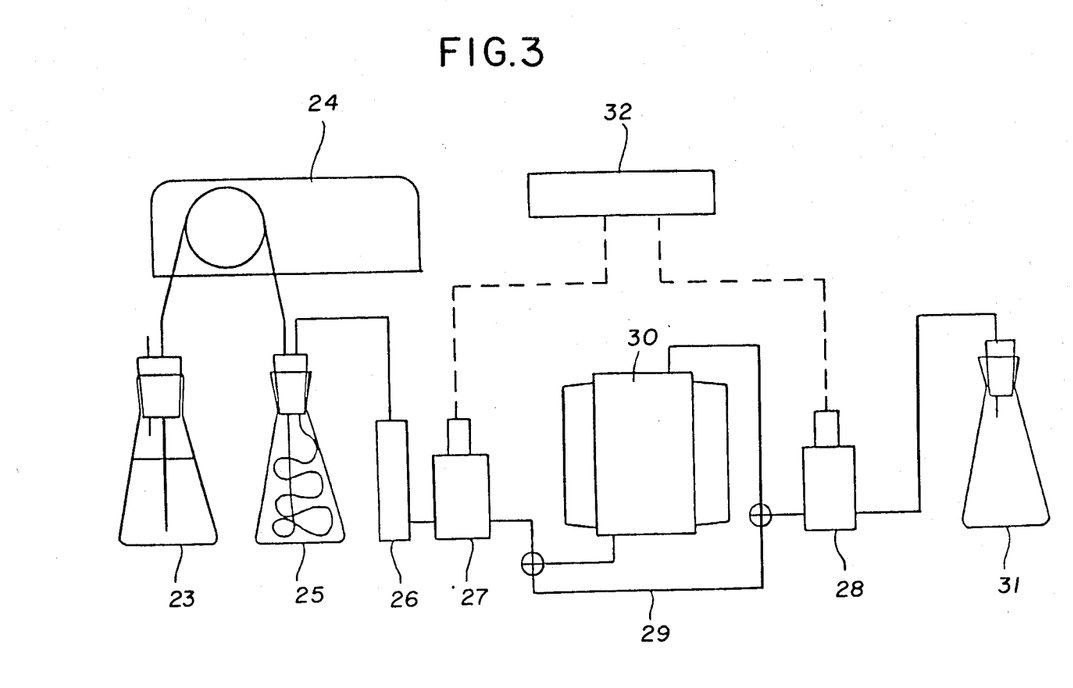
FIG. 3 shows a schematic view of oxygen-measuring equipment.

FIG. 3 shows schematically the layout of equipment for measuring oxygen gas. In the figure, 23 is a container, 24 a pump, 25 a means for oxygenation of the medium via a silicon tube, 26 an air-lock, 27,28 oxygen gas electrodes of Clark type, 29 a calibration loop, 30 an cultivation chamber (double), 31 a collecting vessel for used medium and 32 a printer with amplifier unit.

Figure 4:
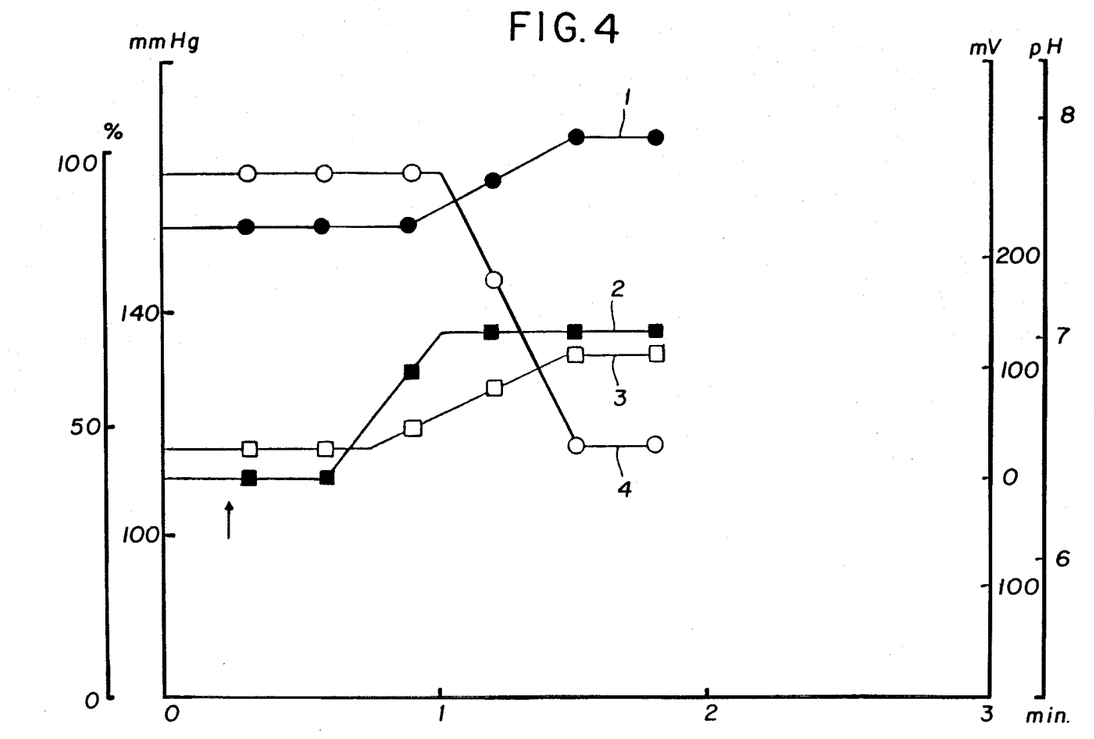
FIG. 4 shows examples of physical measurement parameters.

FIG. 4 shows examples of physical parameters which can be introduced in a multi-parametric system. The figure shows changes measured once complete cell death has occurred. An arrow indicates the addition of toxic substance.

The curves denote:
1: pH
2: $DO_2$
3: ORP
4: Trypan

Figure 5:
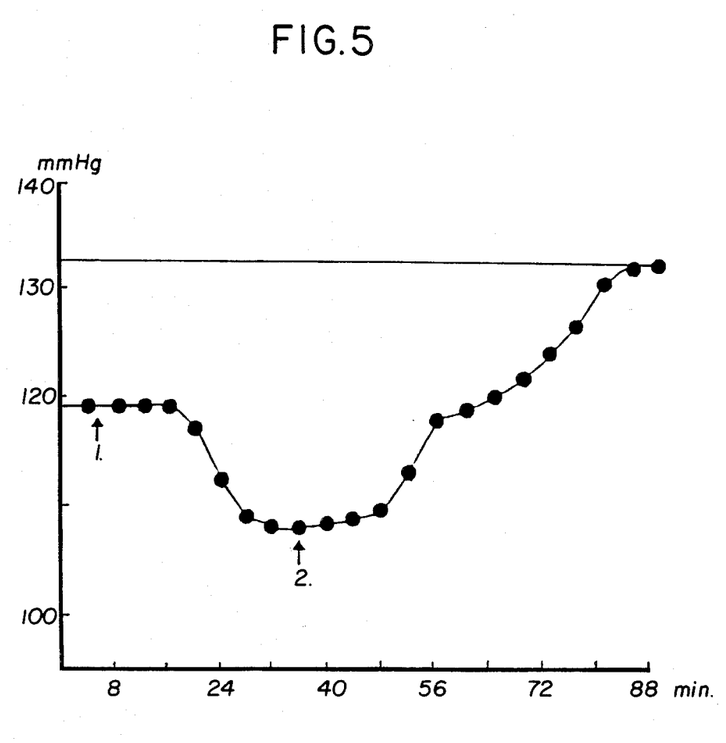
FIG. 5 shows the effect of adding hexachlorophene.
Figure 6:
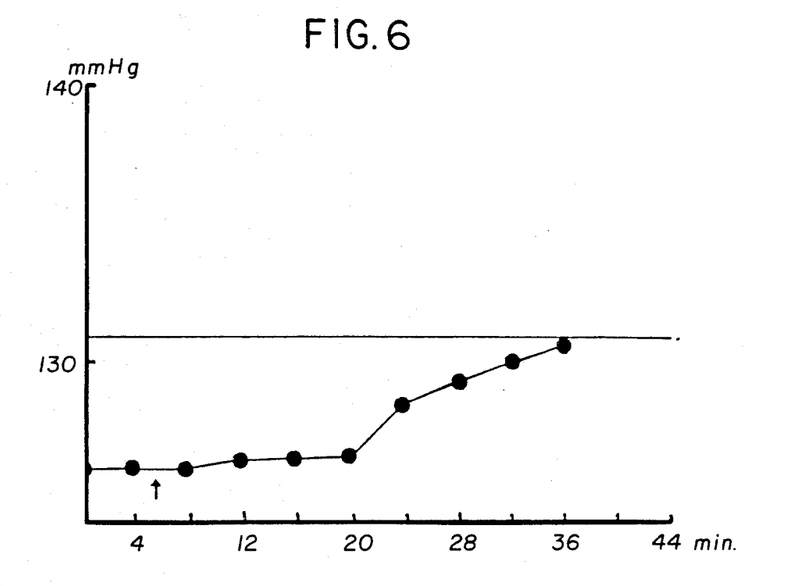
FIG. 6 shows the effect of adding KCN.

The effect of the addition of hexchlorophene on the oxygen gas consumption can be seen in FIG. 5, and FIG. 6 shows the effect of the addition of KCN on the oxygen gas consumption.

Figure 7:
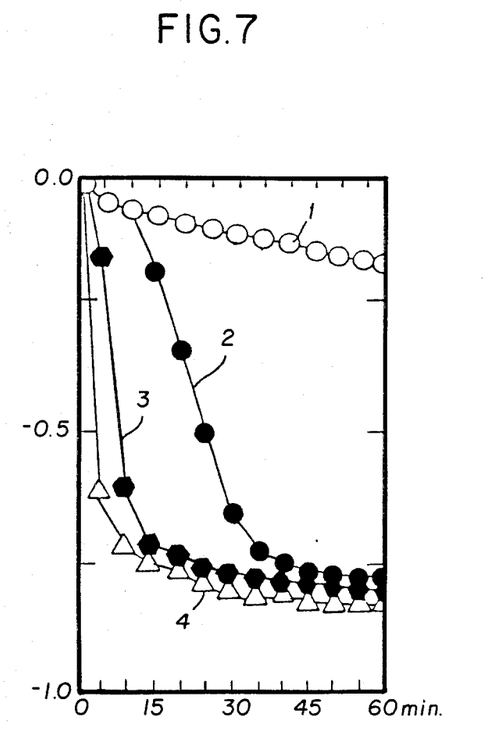
FIG. 7 shows the effect of Triton X-100 on the outflow of $^3H$-2-deoxy-D-glucose.

FIG. 7 shows the effect of Triton X-100 on the outflow of $^3H$-2-deoxy-D-glucose from cultivated neutroblastoma cells in the perfusion system. The curves specify control (1), 0.015% (2), 0.022% (3) and 0.03% Triton (4).

The y-axis log in the diagram indicates remaining activity in % of the total.

The parameters which can be used to study the state of the cells during perfusion are primarily:
$DO_2$ see FIGS. 4 and 5
pH see FIG. 4
Redox potential see FIG. 4.

Examples of other parameters which can be used are ATP (adenosine triphosphate) content and LDH (lactate dehydrogenase) activity in the perfusion liquid. These function as indicators of membrane leakage and their concentration can be expected to increase after exposure. Another way of measuring membrane leakage is to study the outflow of an isotope-marked marker (see Example 5). It is also possible to measure the absorption of trypan blue in dead cells with the help of light absorption (see Example 4 and FIG. 4).

The invention will now be described in more detail with the help of the following examples.

EXAMPLE 1

Comparison between perfusion culture in the cell described above and an unperfused culture The cell line used is Neuroblastoma C1300, substrate

| F10 according to Ham, R. G. Exp Cell Res, 29 (1963) p 515 | 87% |
| --- | --- |
| Calf serum | 9% |
| Foetal calf serum | 4% |

The perfusion was carried out in a recirculated system with a perfusion volume of 100 ml. The perfusion rate was 1 ml/min. The cultures were checked in a microscope during the perfusion period. After 7 days the concentration of cells in the perfused dishes was 14 times the original concentration. The equivalent figure for the control cultures, i.e. unperfused cultures was 6 times.

No signs of the growth curve starting to flatten out could be detected in the perfusion cultures. Growth had ceased in the control cultures, however. When the experiment was discontinued, the number of cells per $cm^2$ was 350,000 in the perfusion culture.

EXAMPLE 2

The effect of hexachlorophene on the oxygen gas consumption in neuroblastoma cells Cell line and substrate as in Example 1.
Hexachlorophene was added on two occasions, marked in FIG. 5. Six minutes after measurement 2.5

μg/ml (1) was added and after another 30 minutes 25 μg/ml (2).

The experiment layout is shown in FIG. 3 and the pump rate of 1 ml/min. The experiment indicates that the system regulates the $O_2$ absorption in the cells in an extremely sensitive manner.

EXAMPLE 3

The effect of adding potassium cyanide on the oxygen gas consumption in neuroblastoma cells Cell line and substrate as in Example 2. The culture volume and pump rate as in Example 1. 1mM KCN was added 5 minutes after measuring was started. The result can be seen in FIG. 6.

EXAMPLE 4

Determining $LD_{50}$ values by means of cell death, measured as absorption of trypan blue The accumulation of trypan blue (a stain which is taken up in dead cells) can be calculated with the help of light-absorption measurements. It has been found that cell death in neuroblastoma cells correlates well with the $LD_{50}$ values obtained from animal experiments for the following tested substances: acetone, benzene, n-butanol, t-butanol, dioxane, n-propanol, $HgCl_2$, $CH_3HgCl$, $CdCl_2$, $K_2Cr_2O_7$ and pp-DDT.

A correlation coefficient of 0.98 was obtained upon comparison.

EXAMPLE 5

Leakage of $^3H$-2-deoxy-D-glucose from cultivated cells as a measurement of membrane damage The substance 2-deoxy-D-glucose (2DG) is taken up by the cell over the membrane via a specific transport system. Inside the cell, 2DG is converted in such a way that its ability to pass through the cell membrane is drastically reduced. This means that if cultivated cells are placed in a solution containing radioactively marked 2DG, the radioactivity will be enriched in the cells, whereas cells in which the membrane has been damaged due to the presence of (milieu-)toxic substances, will release 2DG into the solution again. The radioactivity collected in the cell will then decrease. The degree of reduction can be taken as a measurement of the extent of cell membrane damage. This fact has been utilized in the present method. After being allowed to absorb radioactive 2DG for two hours, the radioactivity not absorbed was washed off, and the cells placed in the perfusion system and perfused at a rate of 1 ml/min. The perfusate was collected with the help of a fraction collector which changes collecting vessel every fifth minute. When the radioactivity was measured in the perfusion liquid it was found that the activity leaks slowly out of the cells. The detergent Triton X-100 was used as model substance for membrane-damaging substances and it was found that the outflow of radioactivity from cultivated neuroblastoma cells increases in the presence of Triton. The extent of the increase is correlated to the Triton concentration (see FIG. 7).

We claim:

1. Apparatus for perfusion-cultivation of at least one cell culture of human or animal origin, comprising a cylindrical body terminating at least one end in a truncated conical body having an end surface recessed from the end of said truncated conical body, means extending through said cylindrical body and through the periphery of said end surface for supplying a nutrient medium to the cell culture, and means connected through said cylindrical body and through the opposite periphery of said end surface for removal of the nutrient medium from the cell culture, whereby the cell culture is subjected to a substantially laminar flow of medium, wherein said truncated cone being configured to directly receive a cell culturing dish having an inner diameter substantially the same as the outer diameter of said truncated cone thus forming a cell culturing chamber bounded by the bottom surface of the dish, the recessed end surface of said truncated cone, and the inner walls of the cone.

2. Apparatus according to claim 1 wherein said cylindrical body terminates at both ends in a truncated conical body, and wherein said means for removal of the nutrient medium through the periphery of one said end surface and said means for supplying a nutrient medium through the periphery of the other said end surface comprises a common tube means which forms an angle of about 50° to 55° with a plane perpendicular to the axis of said cylindrical body.

3. Apparatus according to claim 1 or 2, wherein said body comprises a transparent material.

4. Method for perfusion cultivation of at least one cell culture of human or animal origin comprising the steps of:
    (a) introducing a cell culture into a cell culture dish;
    (b) transferring said dish to an apparatus comprising a cylindrical body terminating at at least one end in a truncated conical body having an end surface recessed from the end of said truncated conical body, means extending through said cylindrical body and through the periphery of said end surface for supplying a nutrient medium to the cell culture, and means connected through said cylindrical body and through the opposite periphery of said end surface for removal of the nutrient medium from the cell culture, wherein
    said truncated cone being configured to directly receive a cell culturing dish having an inner diameter substantially the same as the outer diameter of said truncated cone, thus forming a cell culturing chamber bounded by the bottom surface of the dish, the recessed end surface, and the inner walls of the cone;
    (c) filling said cell culturing chamber with nutrient medium through said means for supplying and removing said nutrient medium through said means for removing, thereby subjecting said cell culture to a substantially laminar flow of nutrient medium.

5. Method according to claim 4, wherein said cell culture comprises neuroblastoma cells.

6. Method according to claim 4 or 5, further comprising the steps of determining the effect of a test substance added to the nutrient medium by measuring the variation in oxygen consumption of said cells.

7. Method according to claim 4 or 5, further comprising the steps of determining the effect of a test substance added to the nutrient medium by measurng the variation in the number of living cells.

8. Method according to claim 7, wherein a suitable coloring agent is added to said cells, and the variation in the number of living cells is measured by relating the number of dead cells to the absorption of light.

9. Method according to claim 8, wherein said suitable coloring agent is trypan blue.

10. Method according to claim 4 or 5, further comprising the steps of determining the effect of a test substance added to the nutrient medium by measuring the variation in the value of the pH of the nutrient medium resulting from passage through the cell culture.

11. Method according to claim 4 or 5, wherein a variation in the redox potential of said nutrient medium resulting from passage through the cells is measured.

12. Method according to claim 4, wherein prior to said cultivation, the cells to be cultured are treated with a solution containing a radioactively labelled compound which is taken up and concentrated by the cells, and determining the effect of a test substance added to the nutrient medium by measuring the increase in the release of radioactive material from the cells into the nutrient medium due to the addition of a test substance to the substrate and the toxicity of the substance is related to that increase.

13. Method according to claim 12, wherein said radioactively labelled compound is $^3$H-2-deoxy-D-glucose.

14. Method according to claim 4 further comprising the steps of determining the effect on the cell culture of a test substance added to the nutrient medium by measuring parameters indicative of the state of the cells.

* * * * *